(12) United States Patent
Habiba et al.

(10) Patent No.: US 9,931,609 B1
(45) Date of Patent: Apr. 3, 2018

(54) ANTIBACTERIAL ACTIVITY OF SILVER-GRAPHENE QUANTUM DOTS NANOCOMPOSITES AGAINST GRAM-POSITIVE AND GRAM-NEGATIVE BACTERIA

(71) Applicants: Khaled Habiba, San Juan, PR (US); Vladimir Makarov, San Juan, PR (US); Brad R Weiner, San Juan, PR (US); Gerardo Morell, San Juan, PR (US)

(72) Inventors: Khaled Habiba, San Juan, PR (US); Vladimir Makarov, San Juan, PR (US); Brad R Weiner, San Juan, PR (US); Gerardo Morell, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 15/096,235

(22) Filed: Apr. 11, 2016

Related U.S. Application Data

(60) Provisional application No. 62/145,559, filed on Apr. 10, 2015.

(51) Int. Cl.
*B82Y 5/00* (2011.01)
*B01J 19/12* (2006.01)
*A61K 33/38* (2006.01)
*A61K 47/48* (2006.01)
*B82Y 40/00* (2011.01)

(52) U.S. Cl.
CPC ............ *B01J 19/121* (2013.01); *A61K 33/38* (2013.01); *A61K 47/48215* (2013.01); *A61K 47/48884* (2013.01); *B82Y 5/00* (2013.01); *B82Y 40/00* (2013.01); *Y10S 977/734* (2013.01); *Y10S 977/847* (2013.01); *Y10S 977/915* (2013.01)

(58) Field of Classification Search
USPC .................................................. 556/110, 112
See application file for complete search history.

(56) References Cited

U.S. PATENT DOCUMENTS

2012/0265122 A1* 10/2012 El-Shall ............ A61K 41/0052
604/20

* cited by examiner

*Primary Examiner* — Pancham Bakshi
(74) *Attorney, Agent, or Firm* — Hoglund & Pamias, PSC; Roberto J. Rios

(57) ABSTRACT

The invention provides a composite of silver nanoparticles decorated with graphene quantum dots (Ag-GQDs) using pulsed laser synthesis. The nanocomposites were functionalized with polyethylene glycol (PEG). A concentration of 150 μg/mL of Ag-GQDs, a non-toxic level for human cells, exhibits strong antibacterial activity against both Gram-Positive and Gram-Negative Bacteria.

18 Claims, 12 Drawing Sheets

ANTIBACTERIAL ACTIVITY OF SILVER-GRAPHENE QUANTUM DOTS NANOCOMPOSITES AGAINST GRAM-POSITIVE AND GRAM-NEGATIVE BACTERIA

GOVERNMENT INTEREST

The claimed invention was made with U.S. Government support under grant numbers 1002410 and 0841338 awarded by the National Science Foundation (NSF) and grant number NNX13AB22A awarded by the National Aeronautics and Space Administration (NASA). The government has certain rights in this invention.

BACKGROUND OF THE INVENTION

Microbial infections are considered a major health problem with a growing concern toward those that do not respond to treatment due to antibiotic-resistant bacteria. According to the U.S. Centers for Disease Control and Prevention, approximately two million people are infected annually with bacteria resistant to antibiotics, of which ca. 23000 people die as a direct result of these infections. The prevention and treatment of these infections has drawn considerable attention and presents a critical challenge to develop drugs, antibiotics and/or antibacterial substances able to inhibit bacterial growth.

Infections due to Gram-negative *Pseudonomas aeruginosa* (*P. Aeruginosa*) and Gram-positive *Staphylococcus aureus* (*S. aureus*) have been documented in surgical sites, where they have been attributed to dermal injuries and burn wounds. Gram-negative bacteria are characterized by a lipid-rich outer membrane as well as a plasma membrane and a thin peptidoglycan layer, while Gram-positive bacteria are enshrouded in thicker, more resilient cell walls. This difference in cell wall is important for antibiotic development, since bacterial resistance might be due in part to cell wall composition.

Several conventional antibacterial agents, such as: tetracycline, streptomycin, and sulfonamides, have been developed to inhibit bacterial infections via the formation of biofilms. However, these antibiotics failed to inhibit all types of bacteria and multidrug-resistant strains have appeared due to the pathogen's evolution in counteracting the biocidal action of the agent molecules. Consequently, it is necessary to develop antibiotics that can overcome the limitations of the conventional antibacterial agents and preferably work against both types of bacteria. Interestingly, materials such as: silver nanoparticles, copper oxide, carbon nanomaterials, and metal oxide nanoparticles, have been reported as antimicrobial agents, and have been considered for use in wound infections, and in the clothing industry. In specific, silver is widely recognized for its capacity to kill bacteria. The mechanism of silver as an antibacterial agent is not totally clear, but it includes some possible mechanisms, such as: denaturation of the 30 s ribosomal subunits, inhibition of respiratory enzymes, binding and dimerization of RNA and DNA, and disruption of the outer membrane. Nevertheless, silver has shown high levels of toxicity at adequate concentrations for its antibacterial use.

The synthesis of silver composites might be a potential solution to overcome the negative side effects of silver, but optimizing the concentration of Ag in these composites remains a challenge. One approach to synthesize silver composites is to use carbon-based nanomaterials such as: graphene, carbon nanotubes, and graphene oxide with low concentrations of silver. The synthesis and use of silver-carbon nanotube complexes as antibacterial material has been previously reported. Another study reported that carbon nanotubes might be toxic due to their contamination with metallic catalysts used in their synthesis.

Graphene quantum dots (GQDs) are among the carbon nanostructures that may be good candidates for biomedical applications due to their solubility in aqueous solutions and high biocompatibility. GQDs are nanostructures of graphene in the size range of 2-20 nm with a set of excellent and unique chemical and physical properties. In general, GQDs have no apparent toxicity in vivo, and they have demonstrated high potential for utilization in cellular imaging, as antibacterial material, and drug delivery.

SUMMARY OF THE INVENTION

According to an aspect of the invention, functionalized Ag-GQDs nanoparticles were synthesized and a study of their cell toxicity and antibacterial properties is disclosed.

In accordance to another aspect of the invention, silver nanoparticles are decorated with GQDs, using the resulting Ag-GQDs to be tailored as an efficient and a safe antibacterial material.

In accordance with a further aspect of the invention, the Ag-GQDs inhibited the growth of Gram-positive *S. aureus* and Gram-negative *P. aeruginosa* bacteria.

In accordance with a yet another aspect of the invention, the decoration of silver nanoparticles with GQDs fostered a synergistic effect that enhanced the antibacterial activity of silver and minimized its toxicity.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Synthesis of the Bare GQDs and Ag-GQDs

Bare GQDs were functionalized with polyethylene glycol (PEG) as follows. A 0.25 wt % mixture of nickel oxide powder (Alfa Aesar) and 1.25 wt % of PEG bis (3-aminopropyl) terminated (Sigma Aldrich) in 98.5 wt % benzene (Sigma Aldrich) was irradiated for 45 minutes with a 1064 nm pulsed Nd:YAG laser (Continuum Surelite II, KDP doubling crystal, 10 Hz, 10 ns pulse width). The synthesized GQDs were separated from benzene and the precipitated nickel oxide by centrifugation at 10000 rpm, following dissolution in nano-pure water. Finally, the GQDs solution was purified by using dialysis bags.

Figure 1:
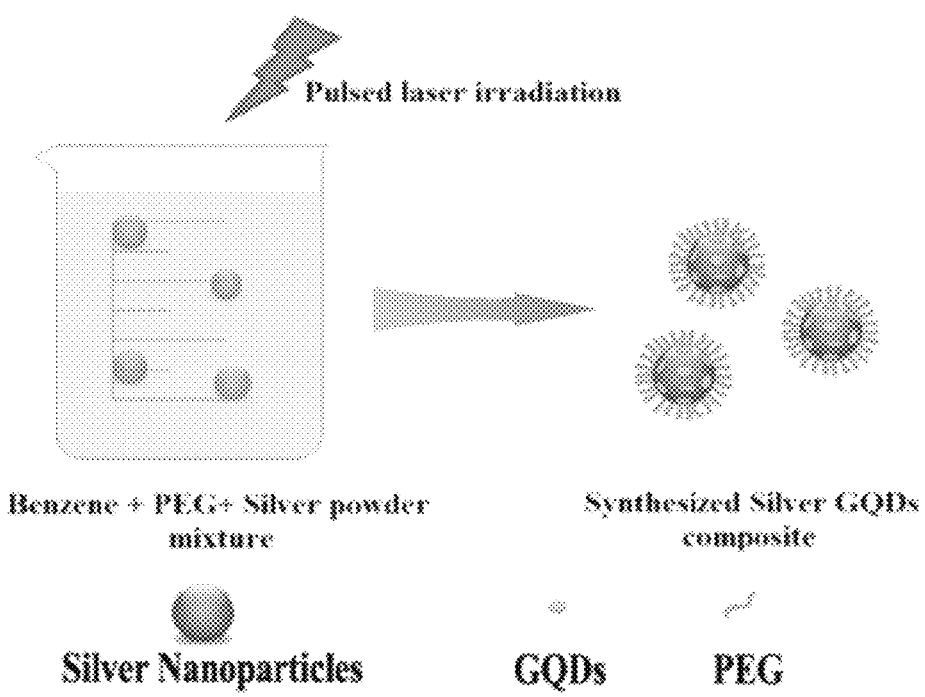
FIG. 1 shows a schematic illustration of the synthesis of Ag-GQDs composite, according to the present invention.

For synthesis of Ag-GQDs, a mixture of 0.25 wt % of silver powder (Sigma Aldrich) and 1.25 wt % of PEG bis(3-aminopropyl) terminated (Sigma Aldrich) in 98.5 wt % benzene (Sigma Aldrich) was prepared and irradiated by pulsed laser, similar to the synthesis of bare GQDs as illustrated in FIG. 1. The synthesized Ag-GQDs nanoparticles were separated from benzene and dissolved in nano-pure water, upon purification by using dialysis bags.

Figure 2:
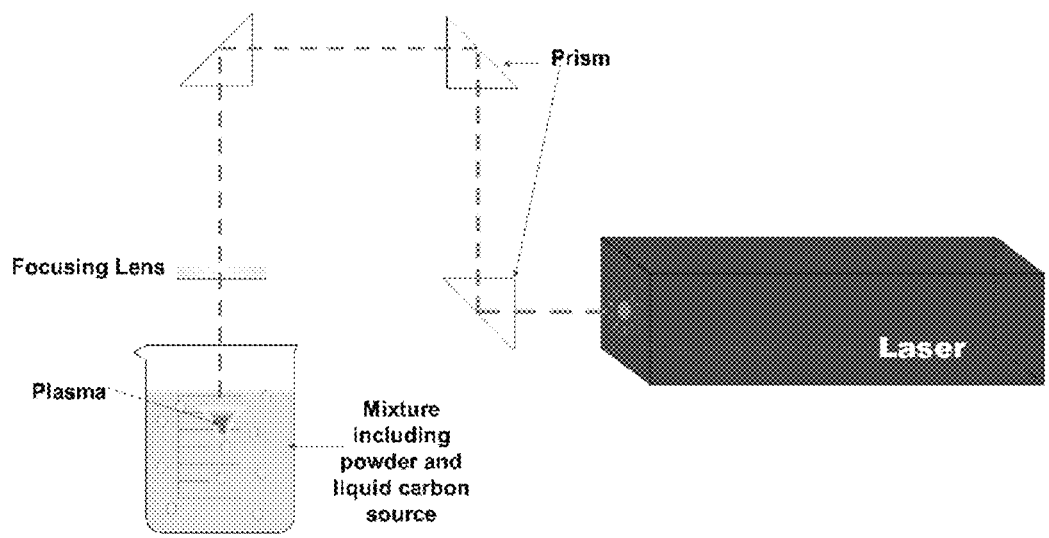
FIG. 2 shows a schematic showing an experimental setup for the synthesis of GQDs nanocomposites by plasma-assisted approach using a pulsed laser, according to the present invention.

In an exemplary embodiment of the invention, 15-100 mg of silver powder, 10-200 mg of PEG bis amino propyl terminated in 8-50 mL of liquid benzene are mixed and sonicated for 5 minutes forming a colloidal suspension of catalysts within the benzene. Then, the suspension is irradiated with high energy pulsed laser for 30-60 minutes at room temperature and atmospheric pressure. The silver particles are maintained suspended under magnetic stirring during irradiation. The suspension changes its color from grey to blackish yellow colloidal suspension. Then, the synthesized nanoparticles are separated from benzene by vacuum evaporation. The nanoparticles powder is dissolved in deionized water, and then sonicated for 1 hour to get a homogenous yellowish solution in water. Finally, the GQDs are purified using dialysis bags. The laser used is Nd:YAG laser with a wavelength of 1064 nm (the laser has a doubling KDP crystal [10% 532 nm green laser and 90% has a wavelength of 1064 nm]) and time duration of pulse is 10 ns (diameter of laser beam in the focusing area is about 0.5 mm). The average energy of laser radiation is in between 25-60 mJ/pulse. Laser radiation power in the maximum of laser radiation pulse varies in between 25-60 MW (repetition rate of laser shots is 10 Hz) range of irradiation time 30-60 minutes, and the time delay between each pulse is 0.1 s. FIG. 2 shows an embodiment of an experimental setup for the synthesis of GQDs nanocomposites by plasma-assisted approach using the pulsed laser.

Instrumentation and Measurements

High transmission electron microscopy (HR-TEM) images were recorded using an electronic microscope (JEOL JEM-2200FS, Japan), operated at 200 kV in STEM mode. Raman Spectroscopy was carried on using a Horiba Jobin-Yvon T-6400 Raman microprobe and a diode Laser with a wavelength of 532 nm. Fourier transform infra-red spectroscopy (FTIR) spectra of the prepared Ag-GQDs/KBr pellets were measured using a FTIR spectrometer (Thermo Nicolet iS50, USA) with pure KBr as the background. XPS experiments were performed with Physical Electronics Instruments (PHI-Quantum 2000, USA), using Al $K_\alpha$ source. The UV-visible spectra were carried on a spectrophotometer (Shimadzu 2550, Japan). XRD patterns were performed with (Rigaku Smart-lab, Japan), equipped with a Cu $K\alpha$ radiation source, at an accelerating potential of 40 kV and a tube current of 44 mA. The XRD samples were prepared by placing a certain powder amount of: bare GQDs, silver, and Ag-GQDs on a silicon substrates. The field emission scanning electron microscope (FE-SEM) micrographs were performed with (JEOL JSM-7500F, Japan), operated at working voltage of 15 kV. Energy-dispersive X-ray spectroscopy (EDS) measurements were employed in the SEM microscope (JEOL 5800 LV, Japan) integrated with EDS detector (Oxford Link ISIS Series), and images for the selected zones were recorded at an acceleration voltage of 20 kV.

Antibacterial Tests

The antibacterial properties of the nanomaterials were tested against Gram-negative P. aeruginosa bacteria (ATCC 27853) and Gram-positive S. aureus bacteria (ATCC 25923). The inoculum for antibacterial assays was prepared from actively growing organisms (logarithmic phase). S. aureus and P. aeruginosa were grown in Mueller Hinton (MH) broth at 37° C. for 24 and 48 hours respectively. Cultures were centrifuged at 3900 rpm using a centrifuge (Eppendorf 5810 R, Germany) for 10 minutes. The pellets were washed twice in PBS and bacterial turbidity was adjusted to the desired concentration. The bacterial concentration was determined by measuring optical density at 600 nm ($OD_{600}$).

The Microdilution Method

The bacterial minimum inhibitory concentration (MIC) for Ag-GQDs and GQDs were determined based on the broth microdilution methods, as described in the Clinical laboratory standards guidelines with minor modifications. MIC is defined as the lowest concentration of an antimicrobial that will inhibit the visible growth of a microorganism after overnight incubation. Briefly, bacterial suspensions were prepared from overnight culture and adjusted to $10^7$ CFU/mL. Then, a 150 µL of fresh MH broth, 20 µL of bacterial suspension and 30 µL of different concentrations of Ag-GQDs and GQDs were added in 96-well plate. A positive growth control of basal medium without nanoparticles was included to evaluate the viability of the tested organisms. Finally, the microplates were incubated at 37° C. for 24 h under static conditions without shaking. The microplates were read before and after incubation at $OD_{600}$ using a microplate reader (Synergy H4 Hybrid).

The Kirby-Bauer Disk Diffusion Method

The antimicrobial susceptibility of Ag-GQDs nanoparticles was evaluated using the Kirby-Bauer disk diffusion method. In brief, a bacterial inoculum with a turbidity equivalent to 0.5 MacFarland was inoculated evenly onto the surface of MH agar in petri dishes by swabbing. Sterile paper disks were saturated with 40 μL solutions of GQDs (1850 μg/mL) or Ag-GQDs (150 and 320 μg/mL) and then deposited on the agar surface. For positive inhibition controls, sterile paper disks were saturated with 40 μL solution containing the antibiotic ampicillin (100 μg/mL) or tetracycline (20 μg/mL) and were used against Gram-positive and Gram-negative bacteria, respectively. The zones of inhibition were measured after 24 hours of incubation at 37° C.

Bacterial Population Growth Rate Assay

The bacterial population growth curves of Ag-GQDs were analyzed using the microplate reader spectrophotometer (Synergy H4 Hybrid). A bacterial inoculum with a turbidity equivalent to 0.5 MacFarland was prepared. Then, 150 μL of fresh MH broth, 20 μL of bacterial suspension and 30 μL of different concentrations of Ag-GQDs (25, 70, 100, 150 and 320 μg/mL) were added in 96-well microplate. For positive growth controls, 30 μL of nanoparticles were replaced with PBS. The reference antibiotic used as negative growth control with Gram-positive bacteria *S. aureus* was ampicillin (100 μg/mL) and tetracycline (20 μg/mL) was used against the Gram-negative bacteria *P. aeruginosa*. Microplates were incubated at 37° C. under linear shaking. The absorbance was measured at $OD_{600}$ at intervals of 20 minutes for a total period of 12-18 hours.

MTS Cell Viability Assay

HeLa cells were cultured in Eagle's minimum essential medium (ATCC) supplemented with 10% fetal bovine serum (ATCC), 100 U/mL penicillin, 100 μg/mL streptomycin and 250 ng/mL amphotericin B (Cellgro) at 37° C. with 5% $CO_2$. The cell viability effects of GQDs and Ag-GQDs nanoparticles were assessed on HeLa cells by using the (3-(4,5-dimethylthiazol-2-yl)-5-(3-carboxymethoxyphenyl)-2-(4-sulfophenyl)-2H-tetrazolium)-based (MTS) CellTiter 96® AQueous Solution Cell proliferation Assay (Promega, USA). $2 \times 10^4$ cells were seeded in 96-well plates (Falcon) and grown overnight. After 24 hours, cell culture medium was removed and 100 μL of complete cell medium containing GQDs (25, 70, 100, 150 and 320 μg/mL) and Ag-GQDs (60, 950, 1850 and 2775 μg/mL) were added. Fresh culture medium was used as a negative control. After 24 hours of cells incubation, medium was discarded and 100 μL of fresh cell medium with 20 μL of MTS reagent was added. Then, cells were incubated for 30 minutes at 37° C. and centrifuged at 2000 g for 10 minutes. Subsequently, the cell medium containing the MTS reagent was transferred to a new microplate and the absorbance at 490 nm was measured with a UV-vis microplate spectrometer (Synergy H4 Hybrid). For data analysis, the results were expressed as % of cell viability. The equation used was the following:

$$\% \text{ of cell viability} = \frac{Abs_{490} \text{ of treated cells}}{Abs_{490} \text{ of untreated cells}} \times 100$$

Half maximal inhibitory concentration ($IC_{50}$) was determined using GraphPad Prism 5 software.

Statistical Analysis

The experiments were performed in triplicates. The results were expressed as the mean of the standard deviation of values obtained from at least three independent experiments, differences in mean between experimental group were analyzed by Student's t-test and ($p<0.05$) was considered statistically significant.

Results and Discussion

Figure 3A:
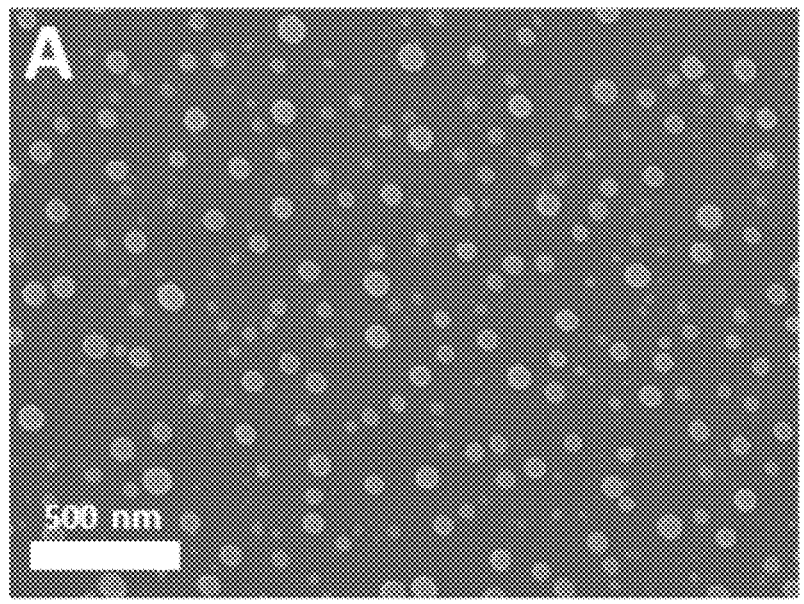
FIGS. 3A and 3B show FE-SEM images of Ag-GQDs, according to the present invention.
Figure 3B:
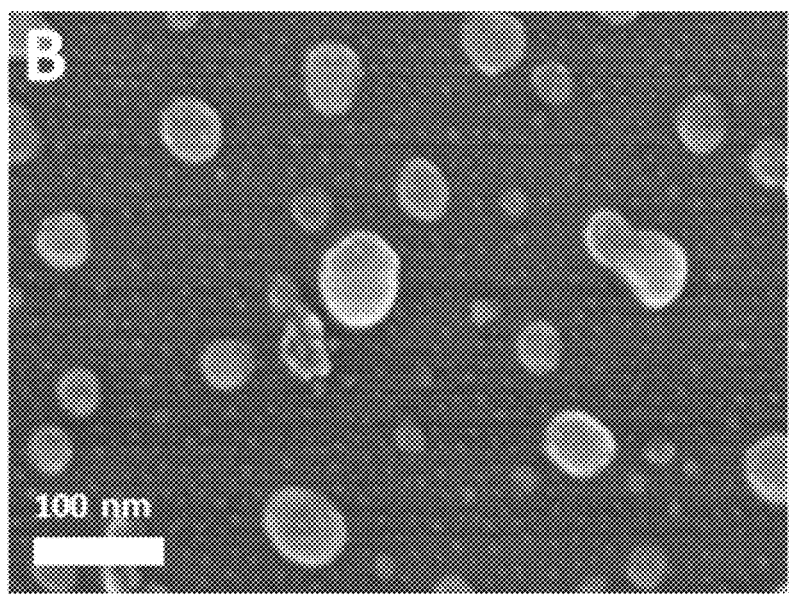
Figure 3C:
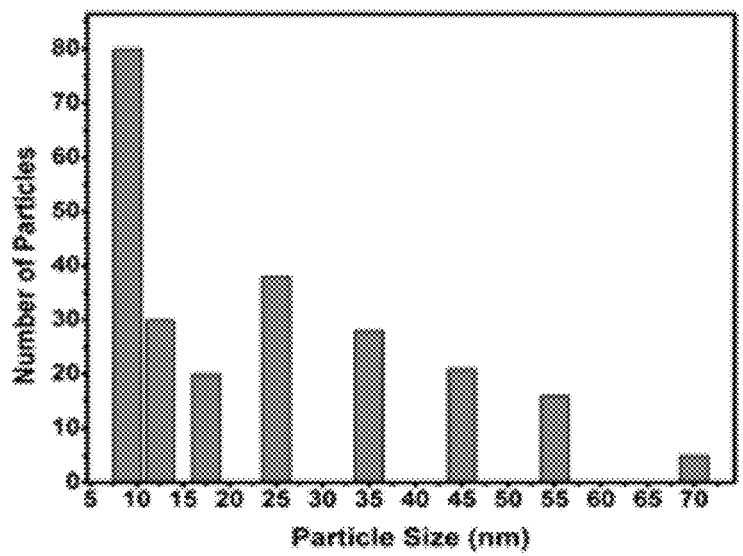
FIG. 3C shows a size distribution histogram of Ag-GQDs, according to the present invention.
Figure 3D:
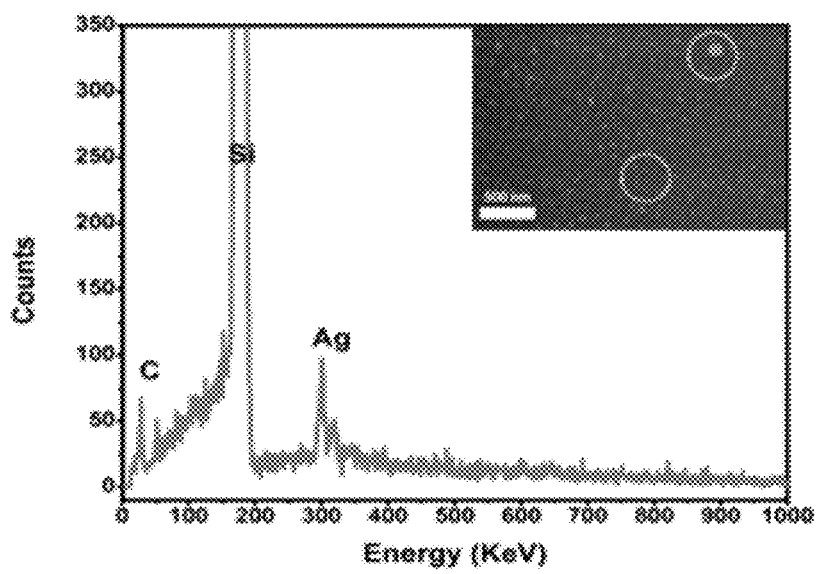
FIG. 3D shows EDS scanned spectrum corresponding to the qualitative elemental composition of Ag-GQDs for the selected regions shown in the inset, according to the present invention.

The synthesized Ag-GQDs nanocomposites were fully characterized using microscopic and spectroscopic techniques, before studying their antibacterial activity. The FE-SEM micrographs in FIGS. 3A and 3B show that Ag-GQDs are in the range of 8-70 nm. The histogram in FIG. 3C depicts the average size distribution of the synthesized nanoparticles, based on the analysis carried out for 5 different fields chosen randomly. FIG. 3D reveals the qualitative elemental composition of Ag-GQDs using the EDS technique, at the selected regions shown in the inset. The EDS spectrum indicates the presence of carbon, silver and silicon. The presence of silver and carbon are attributed to the Ag-GQDs and the silicon peak arises from the substrate, where the nanoparticles were placed for the microscopic characterizations. The data obtained confirm that the synthesized nanoparticles are a composite of carbon-silver.

Figure 4:
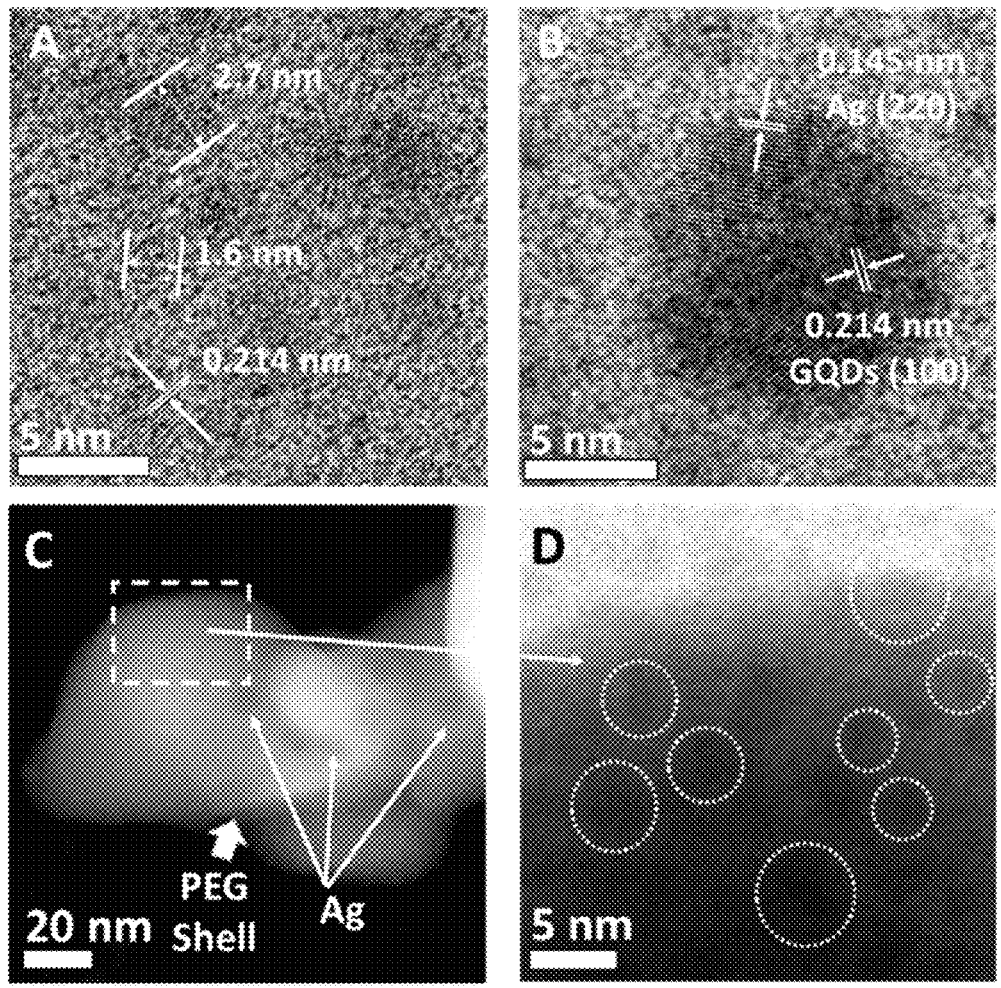
FIG. 4 shows HR-TEM images in scanning mode, according to the present invention.

HR-TEM microscopy was employed to give complementary information related to the size, morphology and crystalline structure of Ag-GQDs, in addition to the FE-SEM data obtained above. The HR-TEM micrographs of bare GQDs in FIG. 4 (image A) depict their size range of 1.6-4 nm, and lattice spacing of 0.214 nm that corresponds to the (100) lattice fringes of graphene. FIG. 4 (image B) displays a single Ag-GQDs nanoparticle. The nanoparticle of the composite shows a diameter of 10 nm with an inter-planar spacing of 0.145 nm that matches with the (220) plane of silver. Some nanostructures were observed on the surface of the silver nanoparticle with a lateral diameter of 1.6-2 nm and the same 0.214 nm inter-planar spacing of graphene (100) shown in FIG. 4 (image A). In order to obtain more information about the composite, we employed the dark field to get the high contrast of the clusters FIG. 4 (image C). The image in the inset of image C shows clusters of nanoparticles in the range of 50-100 nm and other nanoparticles less than 20 nm. It can be clearly observed that the nanoparticles of silver and GQDs are packed together forming the core, which is coated by the PEG shell. FIG. 4 (image D) confirms the presence of bare GQDs inside the PEG shell, when the selected region in the dotted rectangle in image C was magnified. The fact that Ag-GQDs nanoparticles come together in the PEG shell forming clusters explains the wide size distribution observed in the data obtained in FE-SEM images.

Figure 5A:
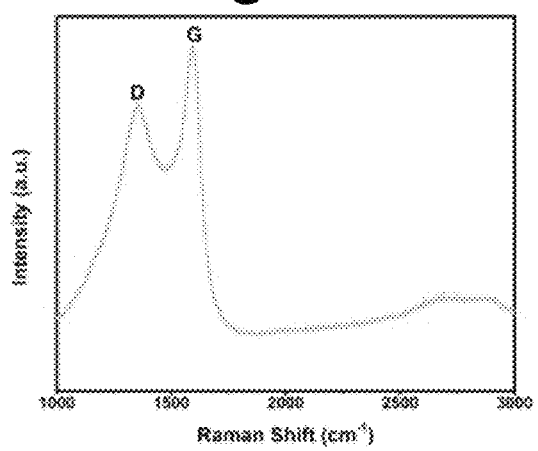
FIG. 5A shows Raman spectrum of Ag-GQDs, according to the present invention.

To characterize the carbon nanostructures synthesized in the nanocomposites, Raman spectroscopy was employed. The Raman spectrum in FIG. 5A shows the presence of D-band at 1353 $cm^{-1}$, which arises from the disorder in $sp^2$ hybridized carbon, and the G-band at 1594 $cm^{-1}$ of the graphitic structures. The spectrum is in good agreement with the spectrum corresponding to synthesized GQDs, reported elsewhere.

Figure 5B:
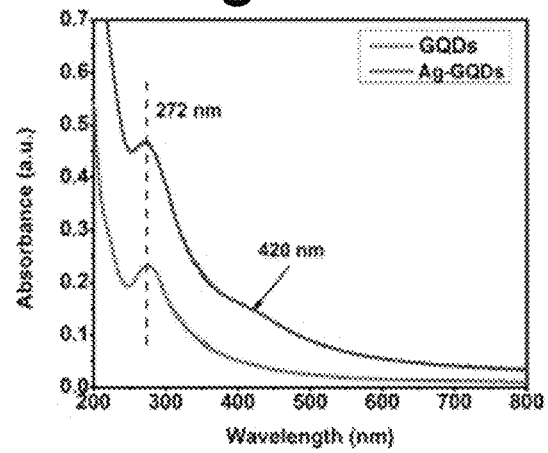
FIG. 5B shows UV-Visible spectra of bare GQDs and Ag-GQDs dissolved in nano-pure water at a concentration of 1 mg/mL, according to the present invention.

UV-Visible spectra of GQDs and Ag-GQDs in FIG. 5B reveal an absorption at ca. 270 nm, which is observed in graphene, and GQDs, and is attributed to π-π* transition of aromatic $sp^2$ domains. The absorption observed in the Ag-GQDs spectrum at ca. 420 nm corresponds to the localized surface plasmon of silver. The UV-Visible data are consistent with the EDS results described above.

Figure 5C:
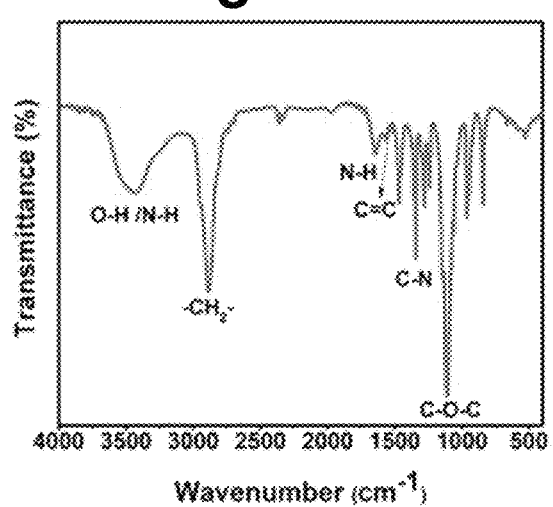
FIG. 5C shows FTIR spectrum of Ag-GQDs showing the characteristic PEG vibrations of C—H and amine groups, and the hydroxyl groups on the surface of Ag-GQDs, according to the present invention.

The conjugation of Ag-GQDs with PEG was further characterized using FTIR spectroscopy. In FIG. 5C, the peaks present in the FTIR spectrum of Ag-GQDs are assigned as follows: 2850-3000 $cm^{-1}$ (—$CH_2$ stretching), 1635 $cm^{-1}$ (N—H bending), 1580 $cm^{-1}$ (C═C aromatic bending), 1460 $cm^{-1}$ (C—H bending), 1107 $cm^{-1}$ (C—O—C stretching) and 600-900 $cm^{-1}$ (N—H wagging). The existence of these vibrations indicates the successful conjugation of Ag-GQDs with PEG. The conjugation of PEG on the surface of Ag-GQDs is important in increasing the stabilization, solubility and biocompatibility of the nanocomposites.

Figure 6:
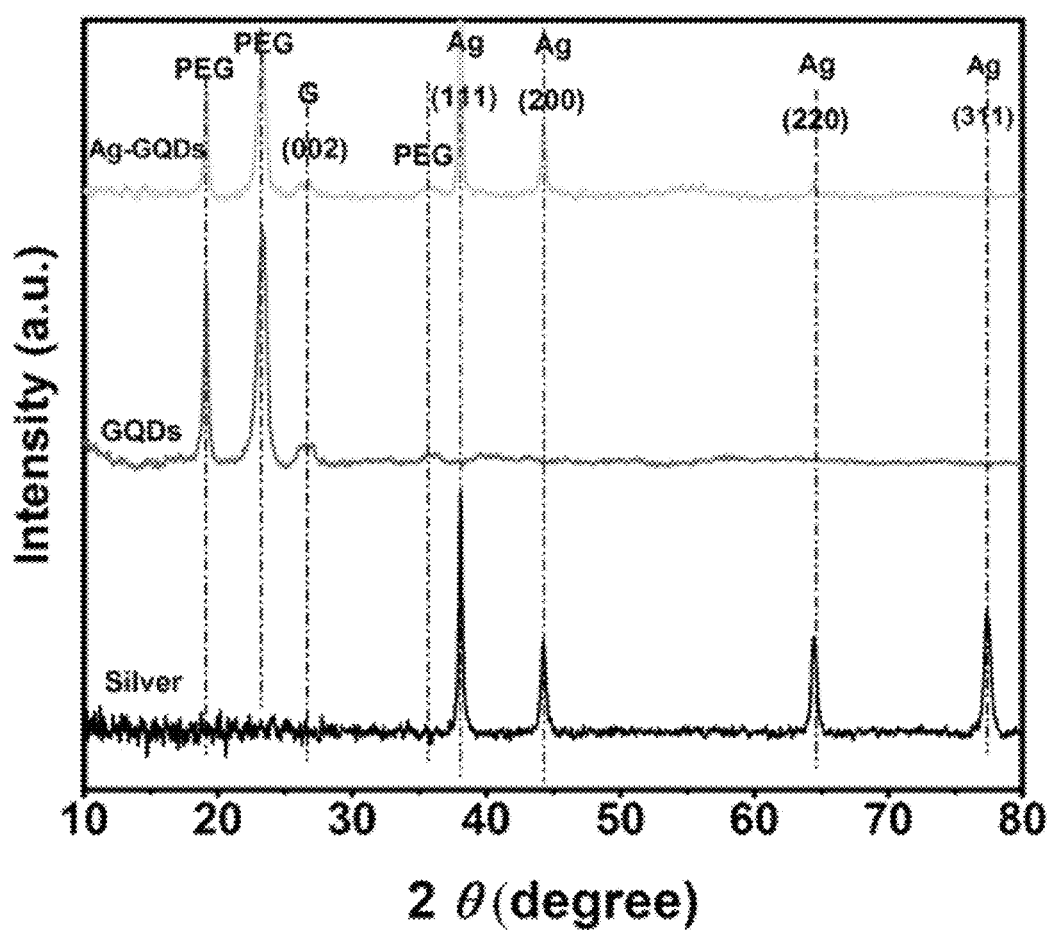
FIG. 6 shows XRD patterns of Ag-GQDs, GQDs and silver powder, according to the present invention.

XRD spectroscopy was analyzed to reveal the crystalline structure of Ag-GQDs and validate the other characterization results. XRD patterns were obtained for the bare GQDs, silver powder used in the synthesis, and the Ag-GQDs (FIG. 6). In the XRD pattern of silver, the peaks at 38.1°, 44.3°, 64.5° and 77.5° are assigned to the crystallographic planes (111), (200), (220) and (311) of the face-centered cubic (fcc) Ag nanoparticles, respectively, according to the JCPDS card No. 04-0783. For the bare GQDs, the peak at 26.6° is commonly observed and corresponds to the d-spacing of the basal plane (002) of graphite. The peaks shown at 18.97°, 23.3° and 35.7° are attributed to PEG, which is conjugated on the surface of bare GQDs, and match with the PEG peaks reported by El Moussaoui et al. As expected, the combination of the observed peaks in silver, PEG and GQDs in the XRD pattern arise in the pattern of Ag-GQDs nanocomposites. The XRD results are consistent with the HR-TEM, UV-Visible, FTIR, Raman and FE-SEM data described above.

Figure 7A:
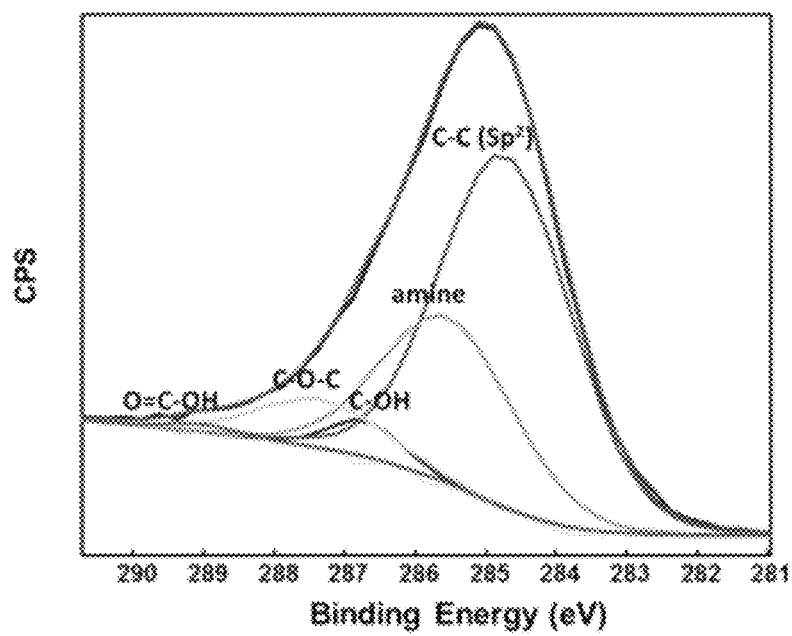
FIG. 7A shows High resolution XPS spectra of Ag-GQDs at C1s, according to the present invention.
Figure 7B:
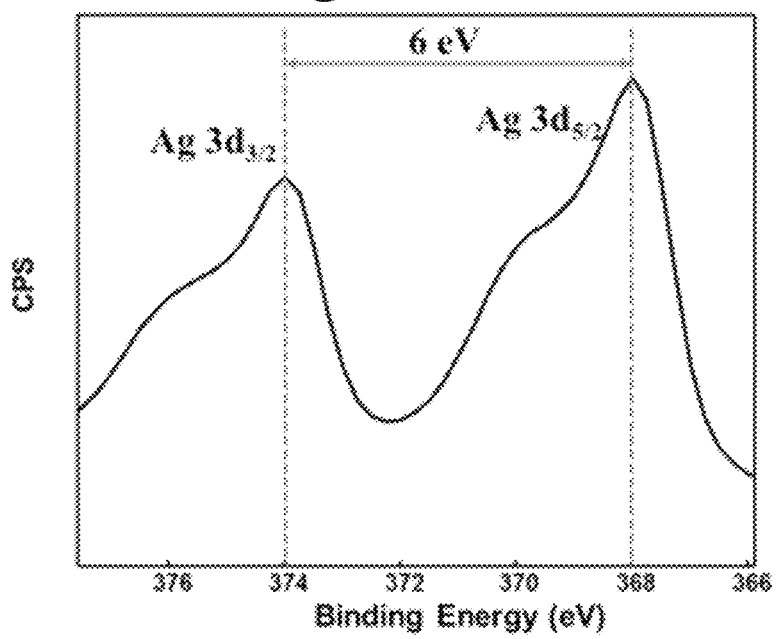
FIG. 7B shows High resolution XPS spectra of Ag-GQDs at Ag3d, according to the present invention.

The XPS technique was employed to quantify the approximate elemental composition attributed from silver and carbon in atomic percent (%). The XPS analyses indicate that the attribution of silver and carbon are approximately 33.4 and 66.6%, respectively. The deconvolution of the high resolution XPS spectrum at C1s in FIG. 7A reveals the presence of amine, hydroxyl, ether and carboxyl groups at 285.7, 286.7, 287.5, 289.0 eV, respectively. FIG. 7B shows the existence of bands at 368 and 374 eV corresponding to Ag3d of the Ag-GQDs. In addition, the difference in binding energy between the peak $Ag3d_{5/2}$ and $Ag3d_{3/2}$ is 6 eV, which confirms that the silver in the nanocomposites is metallic silver. The XPS data are in agreement with the FTIR and XRD data discussed above.

Figure 8:
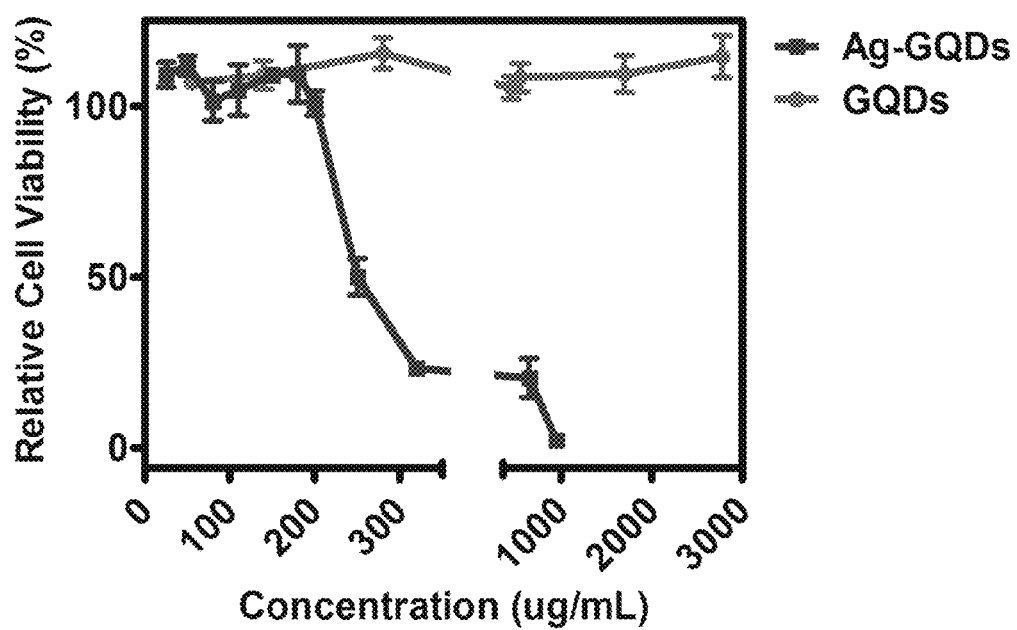
FIG. 8 shows MTS cell viability assay of Ag-GQDs and GQDs in HeLa Cells, according to the present invention.

According to an important aspect of the invention, the Ag-GQDs is synthesized for use in the biomedical field and it is imperative to evaluate their biocompatibility in mammalian cells. The cell viability of HeLa cells at different concentrations of bare GQDs and Ag-GQDs after 24 hours of incubation (FIG. 8) was tested. The results show that cell viability was maintained at 100% for cells incubated with the bare GQDs at concentrations up to 2775 µg/mL (FIG. 8). In the case of Ag-GQDs, they did not affect cell viability at concentrations lower than 200 µg/mL and the $IC_{50}$ is 250 µg/mL. The $IC_{50}$ for Ag-GQDs is around 83.5 µg/mL, which is significantly higher than the $IC_{50}$ values in the range of 1.5-56.4 µg/mL reported for Ag nanoparticles alone. This result indicates that the GQD coating helps to reduce the effective toxicity Ag nanoparticles.

Figure 9:
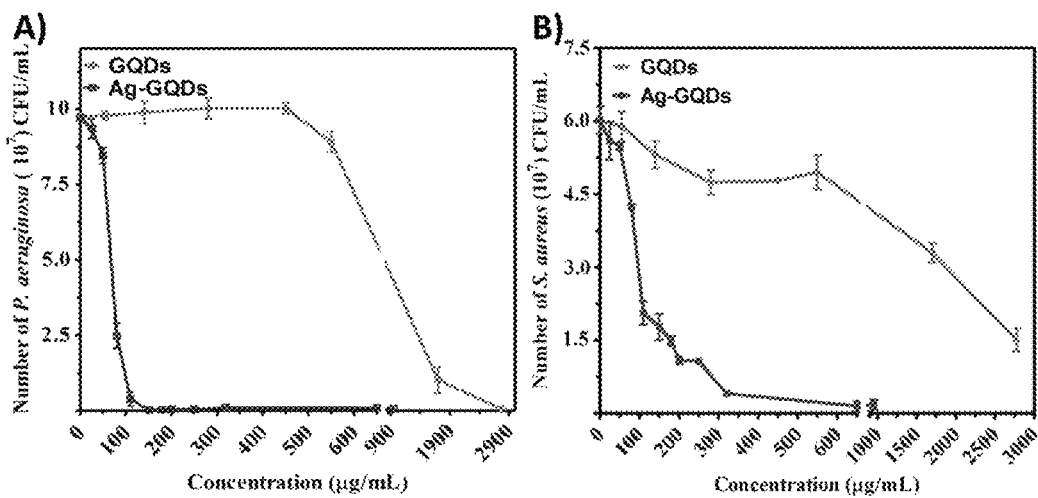
FIG. 9 shows antibacterial activity of bare GQDs and Ag-GQDs at different concentrations after 24 hours of incubation with (A) P. aeruginosa. (B) S. aureus, according to the present invention.

The antibacterial activity of bare GQDs and Ag-GQDs was evaluated at different concentrations against *P. aeruginosa* and *S. aureus* using the microdilution method (FIG. 9). The bacterial inoculum used in this assay was $10^7$ CFU/mL for both bacterial strains, and the concentration of nanoparticles were the same as those used for the mammalian cell viability assays described above. Table 1 below summarizes the MIC values required of bare GQDs and Ag-GQDs to inhibit both bacterial strains. A total inhibition of *P. aeruginosa* was observed when Ag-GQDs and GQDs were used at concentrations of 150 µg/mL and 1850 µg/mL, respectively, as shown in Table 1. On the other hand, the Gram-positive bacteria *S. aureus* showed more resistance to Ag-GQDs and GQDs in terms of the concentrations needed for their total inhibition, i.e. the required concentration of Ag-GQDs was 320 µg/mL and for GQDs higher than 2775 µg/mL (Table 1).

It has been suggested in previous studies that the increment in the resistance of the Gram-positive bacteria could be associated to the thicker cell wall, which protects cells from nanoparticle penetration into the cytoplasm.

TABLE 1

| | MIC (µg/mL) | |
|---|---|---|
| Tested Sample | P. aeruginosa | S. aureus |
| GQDs | 1850 | >2775 |
| Ag-GQDs | 150 | 320 |

Figure 10:
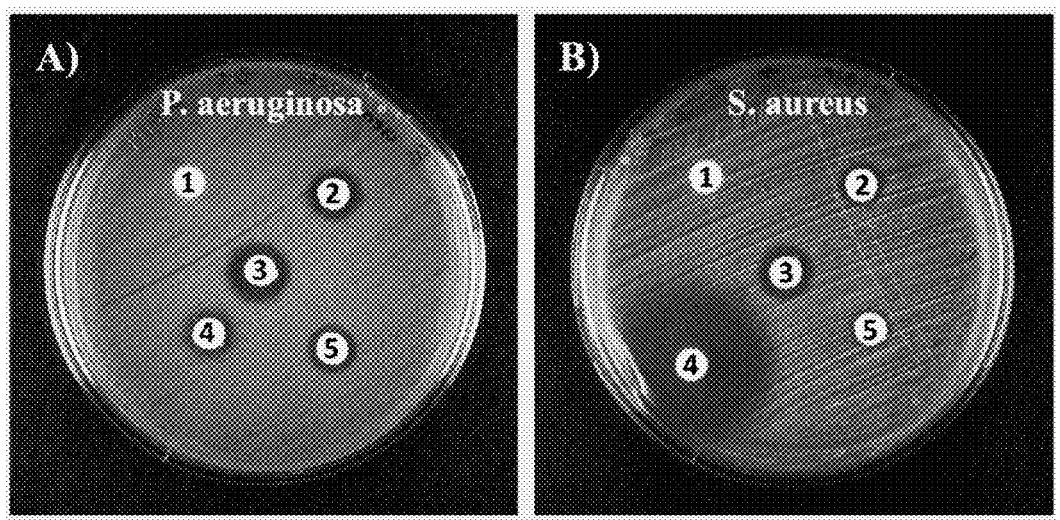
FIG. 10 shows antibacterial activity of bare GQDs and Ag-GQDs against (A) P. aeruginosa. (B) S. aureus, according to the present invention.

Furthermore, the antibacterial activity of Ag-GQDs and bare GQDs was validated using the Kirby-Bauer method as shown in FIG. 10, wherein: (1) Negative Control, (2) Ag-GQDs 150 µg/mL, (3) Ag-GQDs 320 µg/mL, (4) Positive controls: Tetracycline 20 µg/mL in (A) or Ampicillin 100 µg/mL in (B) and (5) GQDs 1850 µg/mL. Table 2 below summarizes the diameter of the inhibition zones exhibited by the diffusion of Ag-GQDs and bare GQDs against *S. aureus* and *P. aeruginosa*, as shown in FIG. 10. In this method, paper disks were impregnated with 40 µL from solutions of Ag-GQDs at concentrations of 150 and 320 µg/mL. Ag-GQDs inhibited both bacterial strains at both concentrations, and the inhibition zones at the lowest concentrations are 10.4 and 9.6 mm for *P. aeruginosa* and *S. aureus*, respectively. In contrast, the bare GQDs exhibited a mild antibacterial behavior against both Gram-positive and Gram-negative bacteria. The Kirby-Bauer data obtained for both Ag-GQDs and GQDs are consistent with the results obtained from the microdilution method. Moreover, both sets of data reveal that GQDs have an intrinsic antibacterial behavior, unlike previous reports which concluded that GQDs can only be used as antibacterial material under specific conditions, such as excitation with 470-nm radiation, or in combination with $H_2O_2$.

TABLE 2

| | Inhibition zone (mm) | |
|---|---|---|
| Tested Sample | P. aeruginosa | S. aureus |
| Negative Control | — | — |
| Ag-GQDs (150 µg/mL) | 10.4 ± 0.1 | 9.6 ± 0.2 |
| Ag-GQDs (320 µg/mL) | 13.2 ± 0.2 | 12.2 ± 0.1 |
| GQDs (1850 µg/mL) | 10 ± 0.1 | 9 ± 0.1 |
| Positive Control | 8.6 ± 0.2 | 35 ± 0.3 |

Figure 11:
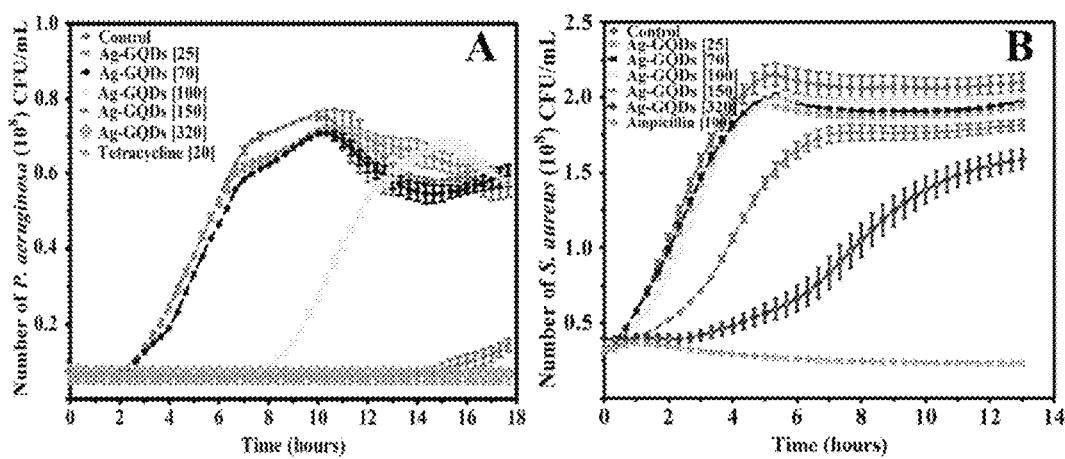
FIG. 11 shows bacterial population growth rate curves of Ag-GQDs incubated with (A) P. aeruginosa (B) S. aureus, according to the present invention.

The results obtained from the microdilution and Kirby-Bauer methods led us to study the inhibition rate of both bacterial strains when treated with Ag-GQDs nanocomposites. The bacterial population growth versus time in the presence of Ag-GQDs was evaluated as shown in FIG. 11. Ag-GQDs nanocomposites induced a delay of 13 hours in the growth time of *P. aeruginosa* for the MIC of 150 µg/mL and a 4 hours delay in the growth time of *S. aureus* at the MIC of 320 µg/mL.

Notably, in all the antibacterial activities experiments to evaluate Ag-GQDs and GQDs, the used inoculum size was in the range of $10^7$-$10^8$ CFU/mL, which is higher than the common inoculum $10^5$ CFU/mL used at routine evaluations of antibiotics. While previous studies showed a similar reduction in the bactericidal properties of antibiotics, and in particular when the size of the inoculum used in the evaluation is ≥$10^8$ CFU/mL, the synthesized Ag-GQDs presented good antibacterial properties against Gram-positive and Gram-negative bacteria.

The present invention provides the successful synthesis of biocompatible nanocomposites of Ag-GQDs. The nanocomposites consists of silver nanoparticles decorated with GQDs on their surface. The Ag-GQDs inhibited the growth of Gram-positive *S. aureus* and Gram-negative *P. aeruginosa* bacteria, which are commonly isolated from microbial infections in wounds. The experiments results showed the successful use of Ag-GQDs in inhibition of both bacterial strains when tested with a bacterial inoculum at high concentration. An optimal concentration of 150 µg/mL would inhibit both types of bacterial growth without affecting mammalian cell viability. The decoration of silver nanoparticles with GQDs fostered a synergistic effect that enhanced the antibacterial activity of silver and minimized its toxicity. These results indicate that Ag-GQDs nanocomposites may be applied as antibacterial material, such as in: antibiotics, coating of surgical instrumentation, wound dressing textiles, disinfectants and detergents.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A method of synthesizing functionalized Nanoparticle-Graphene Quantum Dots nanocomposites (NP-GQDs) comprising:
    irradiating with a source of electromagnetic radiation a mixture containing a compound serving as a source of carbon, a powder serving as a precursor of a nanocomposite core and a ligand source, effectively synthesizing Nanoparticle-Graphene Quantum Dots nanocomposites having a core decorated with Graphene Quantum Dots and functionalized with said ligand.

2. The method of claim 1, wherein ligands are attached to at least one of: the nanocomposite core and the Graphene Quantum Dots.

3. The method of claim 1, wherein the compound serving as a source of carbon is hydrocarbon.

4. The method of claim 3, wherein said hydrocarbon is selected from the group consisting of: benzene, toluene and glycerol.

5. The method of claim 1, wherein the ligand source is a polymer.

6. The method of claim 5, wherein said polymer is selected from the group consisting of: polyethylene glycol (PEG) and polyethylenimine (PEI).

7. The method of claim 1, wherein said powder comprises at least one of: an elemental metal powder, an elemental semiconductor powder, a metal oxide powder and a semiconductor oxide powder.

8. The method of claim 7, wherein the metal is selected from the group consisting of: silver, gold, copper, zinc, cobalt, iron, and ruthenium.

9. The method of claim 7, wherein the semiconductor is selected from the group consisting of: silicon and germanium.

10. The method of claim 1, wherein the compound serving as a source of carbon, the powder and the ligand are combined in a liquid suspension.

11. The method of claim 1, wherein the Nanoparticle-Graphene Quantum Dots nanocomposites are soluble in organic and polar solutions.

12. The method of claim 1, wherein the source of electromagnetic radiation is a laser.

13. The method of claim 12, wherein said laser is an Neodymium-doped Yttrium Aluminum Garnet (Nd:YAG) laser.

14. The method of claim 1, wherein the size of said Graphene Quantum Dots is between 2 and 10 nm.

15. The method of claim 1, wherein the size of said Nanoparticle-Graphene Quantum Dots (NP-GQDs) nanocomposites is between 5 and 100 nm.

16. The method of claim 1, wherein the concentration of the ligand source is between 0.1-10 mg/mL.

17. The method of claim 1, wherein the concentration of the powder is between 0.1-10 mg/mL.

18. The method of claim 1, wherein said mixture is irradiated with a power density between $10^8$-$10^{10}$ W cm$^{-2}$.

* * * * *